(12) United States Patent
Wang

(10) Patent No.: US 7,526,946 B2
(45) Date of Patent: May 5, 2009

(54) CONSTANT-FORCE RHEOMETER

(75) Inventor: Shi-Qing Wang, Streetsboro, OH (US)

(73) Assignee: The University of Akron, Akron, OH (US)

( * ) Notice: Subject to any disclaimer, the term of this patent is extended or adjusted under 35 U.S.C. 154(b) by 218 days.

(21) Appl. No.: 11/581,508

(22) Filed: Oct. 16, 2006

(65) Prior Publication Data

US 2007/0084272 A1    Apr. 19, 2007

Related U.S. Application Data

(60) Provisional application No. 60/726,820, filed on Oct. 14, 2005.

(51) Int. Cl.
*G01N 11/10* (2006.01)
(52) U.S. Cl. .................... 73/54.23; 73/54.37; 73/54.38; 73/54.39
(58) Field of Classification Search ................ 73/54.23, 73/54.37, 54.38, 54.39
See application file for complete search history.

(56) References Cited

U.S. PATENT DOCUMENTS 3,864,961 A * 2/1975 Cessna, Jr. ................. 73/54.23
4,571,989 A   2/1986 Dealy
5,010,130 A * 4/1991 Chapman et al. ............ 524/445
5,417,106 A * 5/1995 Grudzien et al. ........... 73/54.14
6,714,879 B2 * 3/2004 Evans et al. .................... 702/50

OTHER PUBLICATIONS

Dealy, John M., Flow Behavior of Molten Polymers, presented at IUPAC World Polymer Congress MACRO 2004.
Yang, Xiaoping et al., Fast Flow Behavior of Highly Entangled Monodisperse Polymers, Rheol. Acta 37, 415 (1998).
Wang, Shi-Qing, Molecular Transitions and Dynamics at Polymer/Wall Interfaces: Origins of Flow Instabilities and Wall Slip, Adv. Polym. Sci. 138, 227 (1999).
Tapadia, Prashant et al., Nonlinear Flow Behavior of Entangled Polymer Solutions: Yieldlike Entaglement-Disentanglement Transition, Macromolecules, 37, 9083 (2004).

* cited by examiner

*Primary Examiner*—Daniel S Larkin
(74) *Attorney, Agent, or Firm*—Roetzel & Andress; Joseph J. Crimaldi

(57) ABSTRACT

The present invention is generally directed to a method for measuring interfacial stick-slip transitions (SST) and an improved constant-force shear capable of measuring interfacial SST. Some embodiments are capable of measuring SST under simple shear conditions and/or in highly entangled polymer melts. Some embodiments include the application of a constant shearing force to a polymer sample.

10 Claims, 12 Drawing Sheets

Side view          Top view
LVDT

Side view    Top view

CONSTANT-FORCE RHEOMETER

RELATED APPLICATION DATA

This application claims priority from U.S. Provisional Patent Application No. 60/726,820, filed Oct. 14, 2005 and entitled "Improved Constant-Force Rheometer," which is hereby incorporated by reference in its entirety.

This work is supported, in part, by grants from the National Science Foundation (CTS-0115867 and 40596-AC7). The U.S. Government may have certain rights in this invention.

BACKGROUND OF THE INVENTION

The present invention is generally directed to a method for measuring interfacial stick-slip transitions (SST) and an improved constant-force shear capable of measuring interfacial SST. Some embodiments are capable of measuring SST under simple shear conditions and/or in highly entangled polymer melts. Some embodiments include the application of a constant shearing force to a polymer sample.

Hydrodynamic boundary conditions (HBC) play a crucial role in characterization of flow behavior of various fluids. Since the time of Navier and Stokes (see Navier, Mémo Acad Royal Sci Inst France 6, 414 (1823); Stokes, Trans Cam Phil Soc 8, 299 (1845)), the postulate of no-slip or stick HBC has been brought into question. However, the first piece of evidence for slip manifested on macroscopic scales appears to be the publication E. B. Bagley, I. M. Cabott and D. C. West, J. Appl. Phys. 29, 109 (1958), which is based on capillary flow of high density polyethylene. Polymeric fluids are clearly the only single-component materials that exhibit strong violation of no-slip HBC on macroscopic scales.

Recently there has been growing understanding of polymer slip partially reported in the publication F. Brochard and P. G. de Gennes, Langmuir, 3033 (1992). Two types of experimental activities have been carried out to explore the wall slip behavior of entangled polymers on macroscopic scales, see, for example, Y. X. Zhu, S. Granick, Phys. Rev. Lett. 88, 106102 (2002), involving controlled-pressure capillary flow, as well as P. A. Drda and S. Q. Wang, Phys. Rev. Lett. 75, 2698 (1995); S. Q. Wang and P. A. Drda, Macromolecules 29, 4115 (1996); and X. Yang et al., Rheol. Acta. 37, 415 (1998). S. Q. Wang, Adv. Polym. Sci. 138, 227 (1999) discusses simple shear produced in parallel-plates by controlling the speed of one of the two plates, as does L. Leger, J. Phys.—Condens. Mat. 15, S19 (2003). In the former, a stick-slip transition (SST) was observed at a critical pressure, see P. A. Drda and S. Q. Wang, Phys. Rev. Lett. 75, 2698 (1995); S. Q. Wang and P. A. Drda, Macromolecules 29, 4115 (1996); X. Yang et al., Rheol. Acta. 37, 415 (1998). In the latter, the slip velocity was measured as a function of the plate velocity V and found to have smooth dependence on V, see L. Leger, J. Phys.—Condens. Mat. 15, S19 (2003).

The previous studies involving Dao T. T. and L. A. Archer, "Stick-slip dynamics of entangled polymer liquids," Langmuir 18, 2616-2624 and J. M. Dealy, presented at IUPAC World Polymer Congress MACRO 2004, involve a sliding plate shear device, operated in the mode of displacing one of the two surfaces with a controlled speed. More recently Dealy proposed that the origin of the previously reported interfacial SST in capillary flow was a system instability, i.e., an experimental artifact related to the design of the controlled-pressure capillary rheometer. An important question now presents itself as follows. Do entangled polymers undergo a discontinuous interfacial stick-slip transition in viscometric flow? Since it is the interfacial shear stress that determines the nature of the HBC for entangled polymers on solid surfaces, this question must be answered by employing a shearing device where the wall stress is the controlling variable. Because all previous studies were based on sliding plate rheometry that operated in the displacement-controlled mode, they inherently could not provide an answer to the above question.

SUMMARY OF THE INVENTION

The present invention is directed to an improved constant-force shear rheometer, which accommodates the interfacial stick-slip transition (SST) that has been observed to take place in highly entangled polymer melts during simple shear. The discontinuous interfacial stick-slip transition in simple shear flow is determined by the level of chain entanglement. The discontinuous interfacial stick-slip transition takes place in simple shear flow where the shear stress and shear rate are both spatially uniform. The stick-slip transition is accommodated by surface treatment of the shearing plates, adjustments of the plate velocity, and adjustment of the plates' gap distance, between which the samples are sheared.

The present invention also relates to a rheometric device for determining shear rate in an entangled polymer sample that is subject to a stick-slip transition, comprising: a tube having an open end, a closed end, an inside wall and an inside back-wall, wherein the tube comprises two members having semi-circular cross-sections divided along the longitudinal axis of the tube, wherein the tube is capable of receiving a piston at the tube's open end, while maintaining a gap between the inside wall of the tube and the piston, wherein the gap is capable of containing a molten polymer sample; a means for maintaining the polymer sample in a molten state; the piston having a first end and a second end, wherein the first end enters the tube before the second end, and wherein the position and/or speed of the piston is monitored; a means for driving the piston with a known constant force and speed into the tube while the tube contains a molten polymer sample; a means for recording piston speed and/or position as a function of time; and a means for recording the force applied to the piston.

The present invention also relates to a process for making rheometric measurements of entangled polymer samples, comprising: loading a polymer sample into the apparatus as set forth in the preceding paragraph; maintaining the polymer sample in a molten state; driving the piston into the tube at a known speed and with a known constant applied force, so that the polymer sample is forced to flow into the gap between the piston and the tube; calculating the shear rate; and recording the shear rate.

DETAILED DESCRIPTION OF THE INVENTION

Some embodiments of the present invention relate to a constant-force piston shear Rheometer. Some embodiments are useful for taking rheometric measurements of samples that exhibit an interfacial stick-slip transition (SST). Some embodiments enable making such rheometric measurements of highly entangled polymer melt samples under simple shear conditions. The data obtained from these measurements can be dependent on molecular weight, chain structure and/or slip-surface conditions. According to some embodiments, the critical shear stress (i.e. the shear stress at which SST occurs) is a function of chemical structure. For example, some PBD samples exhibit a critical shear stress of about 0.2 MPa, while some PIP samples exhibit a critical shear stress of about 0.1 MPa.

Figure 1A:
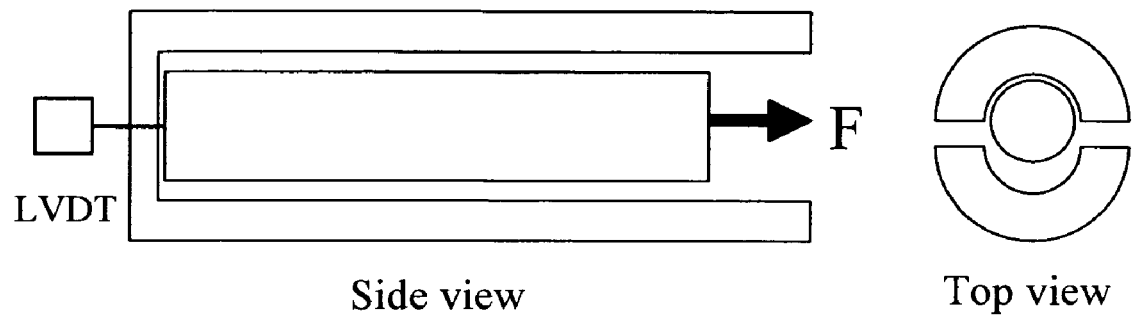
FIG. 1(a) is a schematic depiction of a constant-force shear cell embodying the present invention, which is in a co-cylinder configuration, where the inner cylinder is pulled with a constant force, its speed is measured with a linear variable differential transformer (LVDT), and the outer cylinder is made of two semi-cylinder for the purpose of loading the polymer sample into the gap.
Figure 10:
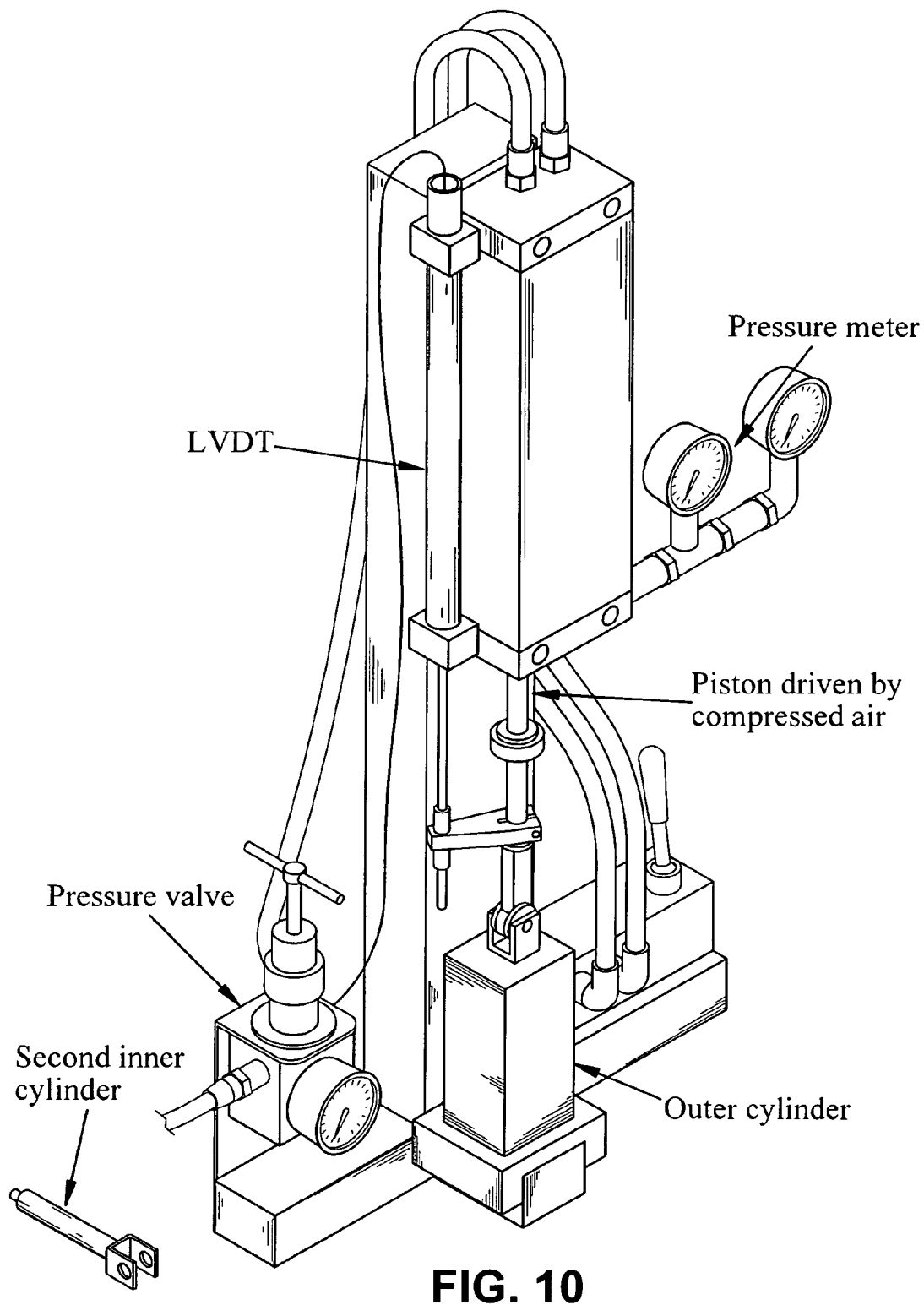
FIG. 10 is a photograph of an instrument embodying the present invention, which is configured for co-cylinder sliding shear, as illustrated in FIG. 1.
Figure 11:
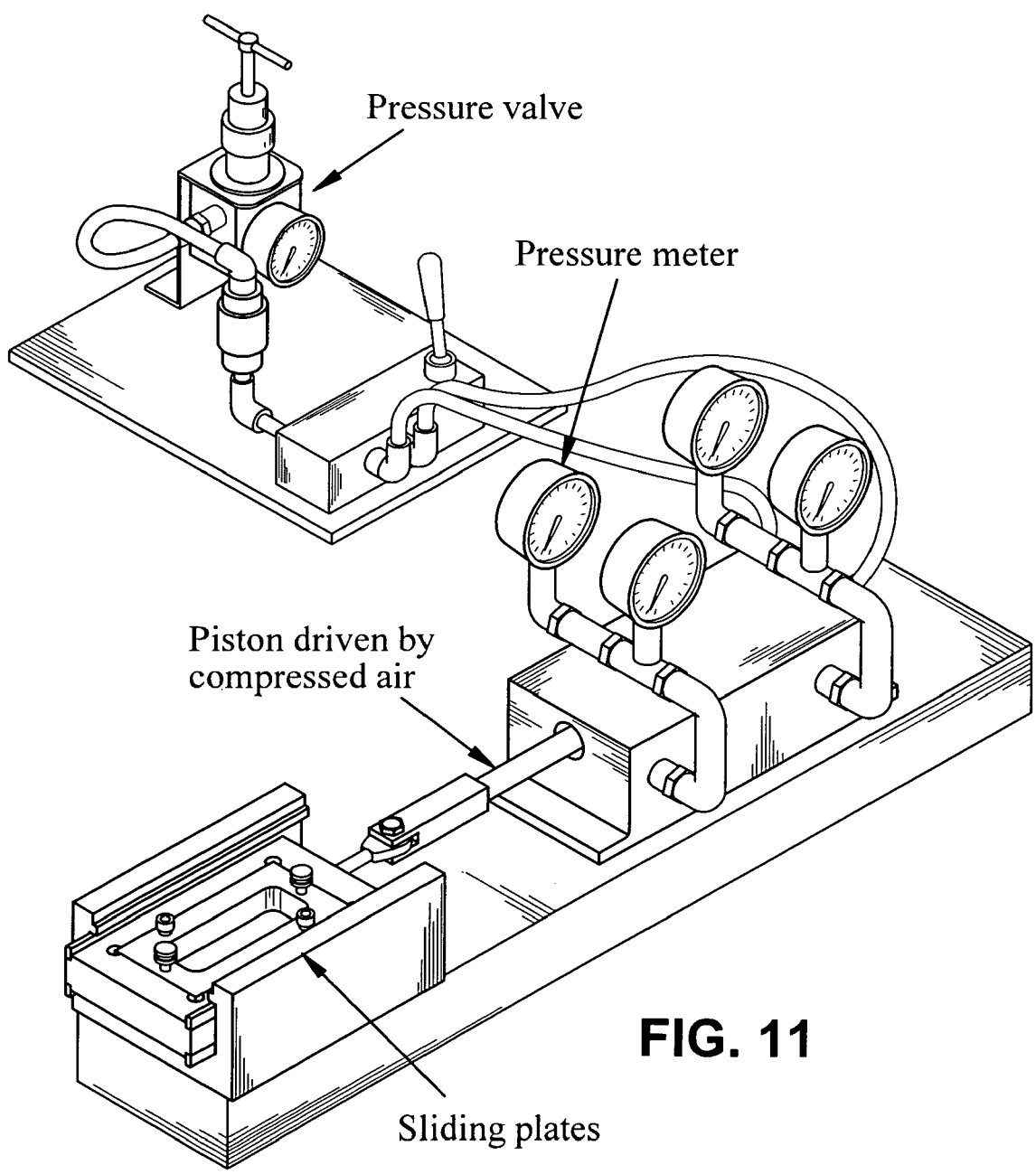
FIG. 11 is a photograph of an instrument embodying the present invention, which is configured for parallel plate linear shear, as illustrated in FIG. 1.

Interfacial shear stress determines the nature of the hydrodynamic boundary condition (HBC) for entangled polymers on solid surfaces. Any violation of the no-slip boundary condition by a shearing apparatus operated in constant force mode needs to be corrected. The present invention is an improved constant-force shear Rheometer. FIG. 1(a) is a drawing of a shear cell in accordance with the present invention. The photographs of FIGS. 10 and 11 show a rheometric apparatus incorporating the cell of FIG. 1. According to this embodiment, the shear stress is calculated according to the total force F exerted on the piston 110 (i.e. on the surface of the inner cylinder). Thus, shear stress is $\sigma$=F/A, where A is the total area of the sample sandwiched between the co-cylinders (110, 120). The total area A is estimated from the total volume of the sample $\Omega$ as A=$\Omega$/h, where h is the gap thickness between the co-cylinders, and $\Omega$ estimated from the mass m, and density $\rho$, of the sample according to the relation m=$\rho\Omega$. In some embodiments, the sample can be linear 1,4-polybutadiene (PBD) having a mass density $\rho$ of about 0.9 g/cm$^3$. The nominal shear rate $\dot{\gamma}$=V/h is measured by tracking the velocity V of the inner cylinder 110 as a function of time while keeping the outer cylinder 120 stationary.

While not wishing to be bound to any one theory, one explanation of no-slip boundary conditions is that the ability of polymeric fluids to exhibit a strong violation arises from a high degree of polymer chain entanglement. In some embodiments, the magnitude of slip can be conveniently characterized in terms of the Navier-de Gennes extrapolation length b according to the following equation:

$$b=(\eta/\eta_i)a \qquad (1)$$

where $\eta$ and $\eta_i$ are the bulk and interfacial shear viscosities respectively, and a is the interfacial layer thickness on a molecular scale. Upon slip, the interfacial layer can have a drastically different viscosity $\eta_i$ compared to that of the bulk viscosity $\eta$.

Figure 1B:
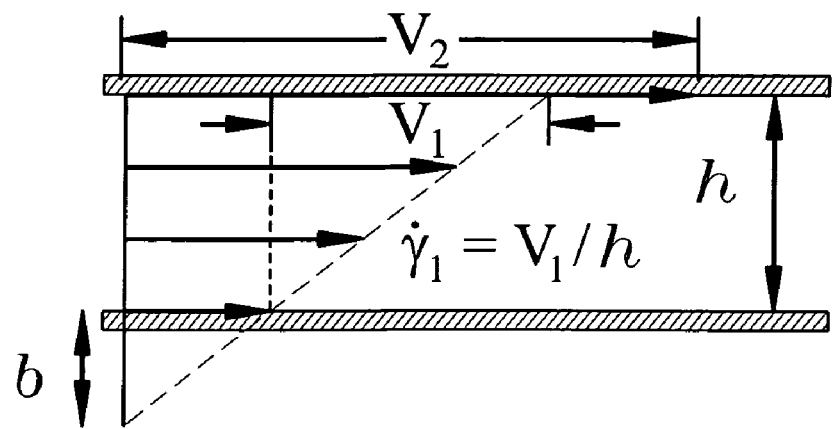
FIG. 1(b) illustrates the presence of wall slip upon the stick-slip transition when the upper plate (corresponding to the inner cylinder) increases its velocity from $V_1$ to $V_2$ without any increase in the internal rate of shear $\dot{\gamma}_1$, where the slip correction is most conveniently quantified by using the extrapolation length b as depicted.

The physical meaning of b is illustrated in FIG. 1(b). According to one theory, in the presence of sufficiently high stresses, entangled polymer chains undergo disentanglement. This produces an interfacial monolayer that is free of entanglement, and therefore has a far lower interfacial viscosity $\eta_i$. According to Equation 1, small values of $\eta_i$ lead to large values of b. This indicates the occurrence of a discontinuous stick-slip transition (SST), i.e. where b jumps from a molecular scale, to a scale as large as many centimeters.

According to one embodiment, an interfacial stick-slip transition can be produced with a known apparatus that has been modified by linearly displacing one of the two parallel surfaces while holding the other one stationary, as shown in FIGS. 1(a) and 1(b). Such linear displacement can produce steady state simple shear flow, provided that it is driven with a constant force. An abrupt stick-slip transition produces a sharp jump in the velocity of the inner cylinder from $V_1$ to $V_2$ at a critical stress $\sigma_c$ such that $$V_2/V_1=\dot{\gamma}_2/\dot{\gamma}_1=1+2b/h \qquad (2)$$

Thus, b can be estimated from based on observed changes in the displacement speed of the inner cylinder at $\sigma_c$.

Figure 2:
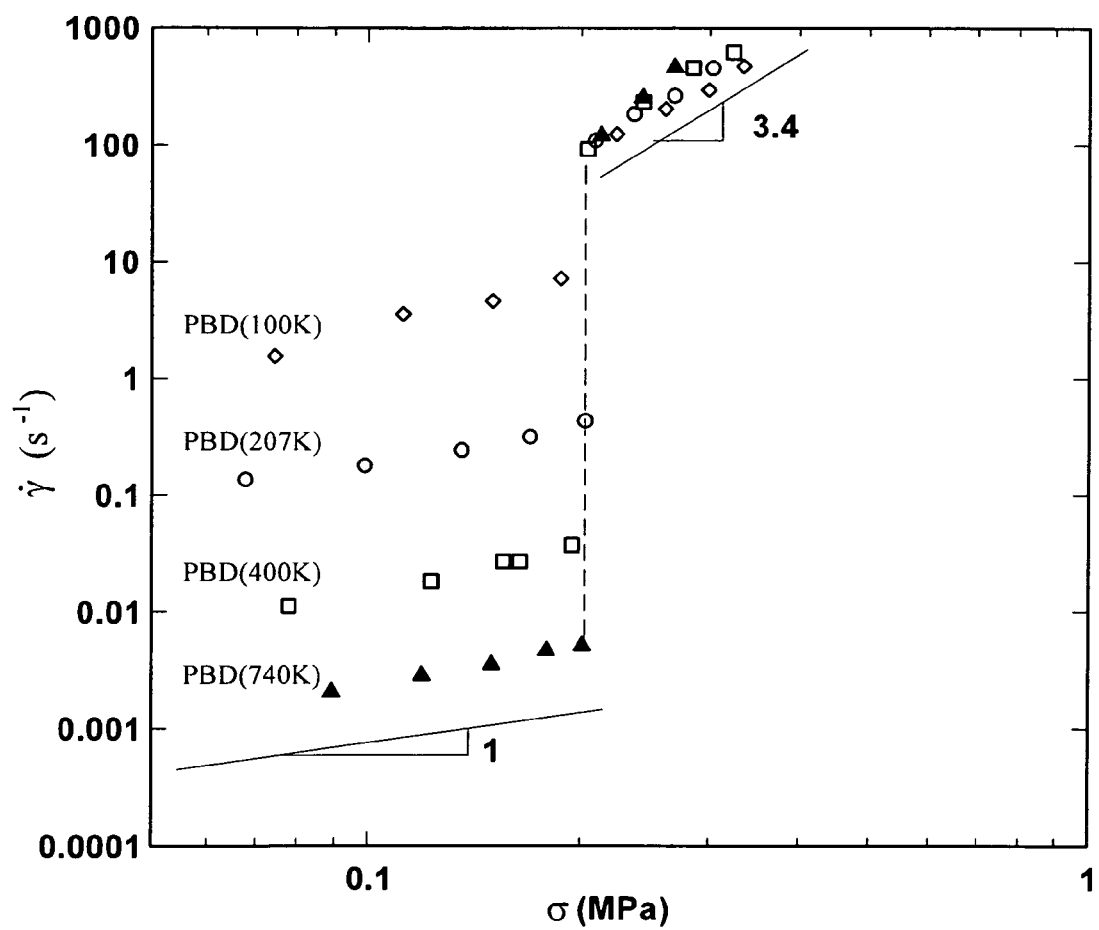
FIG. 2 is a graph of the nominal shear rate, evaluated according to $\dot{\gamma}=V/h$, as a function of the applied shear stress for three 1,4-polybutadiene (PBD) samples of increasing molecular weight (M=100; 207; 410; and 740 Kg/mol), where the gap distance h is around 0.23 mm at T=25° C.

Using the preceding analysis, it is shown that a stick-slip transition (SST) occurs in PBD at about $\sigma$=0.2 MPa, as shown in FIG. 2. In this example, the magnitude of b scales linearly with the bulk sample viscosity $\eta$ and molecular weight M of three monodisperse samples so that b is linearly proportional to $M^{3.4}$. According to this example and Equation 1, the macroscopically large values of b imply that the viscosity ratio $\eta/\eta_i$ is in excess of $10^5$ even for the lowest M of the three samples, assuming a is on the order of the entanglement spacing equal to about 4 nm. Thus, there is chain disentanglement at the interface. While not wishing to be bound to any one theory, the molecular mechanism for the observed SST has been postulated to be stress-induced chain disentanglement. The results in FIG. 2 confirms that Equation 1 can be rewritten as $b=(M/M_e)^{3.4}a$ to describe the transition magnitude, following the empirical 3.4 scaling law governing the molecular weight dependence of $\eta$. Taking the entanglement molecular weight $M_e$ to be 2000 g/mol for PBD and a as the monolayer equal to 4 nm, b is estimated to be on the same order of magnitude as observed experimentally in FIG. 2.

The value of b is also consistent with that obtained previously from the capillary flow studies on nearly the same PBD melts. The fact that the upper slip branch is essentially independent of M arises from the large slip correction (i.e. 2b/h>>1). Equation 2 shows $\dot{\gamma}_2 \approx \dot{\gamma}_1(2b/h) = 2 (\sigma_c/\eta)(\eta/\eta_i)(a/h) = (2\sigma_c/\eta_i)(a/h)$ is independent of bulk viscosity $\eta$ (i.e., of molecular weight M). The second equality follows from substitution of Equation 1 for b.

Figure 3:
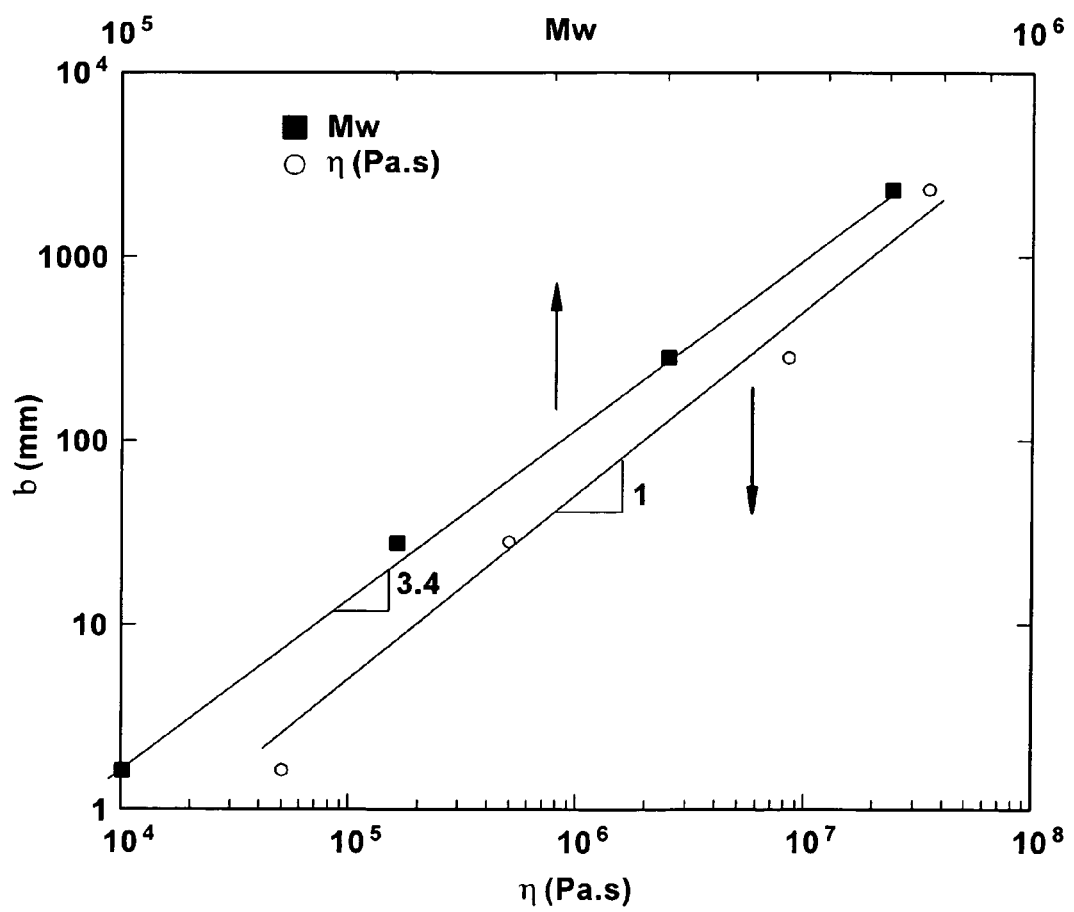
FIG. 3 is a graph of the extrapolation length b (mm) as a function of weight average molecular weight $M_w$ and shear zero viscosity $\eta_0$ at T=25° C. for PBD samples.

In elucidating the interfacial nature of the observed SST, one compares the flow curve obtained with the present apparatus with that from capillary flow rheometry based on a die with diameter D=1.0 mm and aspect ratio L/D=15. FIG. 3 shows that the PBD melt underwent an abrupt transition in both planar Couette shear and pressure-driven capillary flow. This is not unique to capillary flow. Importantly, the critical stress $\sigma_c$ for the transition is significantly higher for capillary flow. Since the lower Newtonian branches overlap well for both flow apparatuses, the difference in $\sigma_c$ is not due to any complications associated with the analysis of capillary rheometry and must be taken seriously.

In some embodiments, a high hydrostatic pressure P, on the order of $P=(4L/D)\sigma_c=1.2\times10^7$ Pa, makes it more difficult for the interfacial chain disentanglement to take place. Thus, the present invention demonstrates for the first time the existence of SST in so called drag flow, and provides the first indication of how hydrostatic pressure postpones the SST. While not wishing to be bound to any one theory, it is plausible that chain adsorption is stronger on steel at high hydrostatic pressures.

Figure 7:
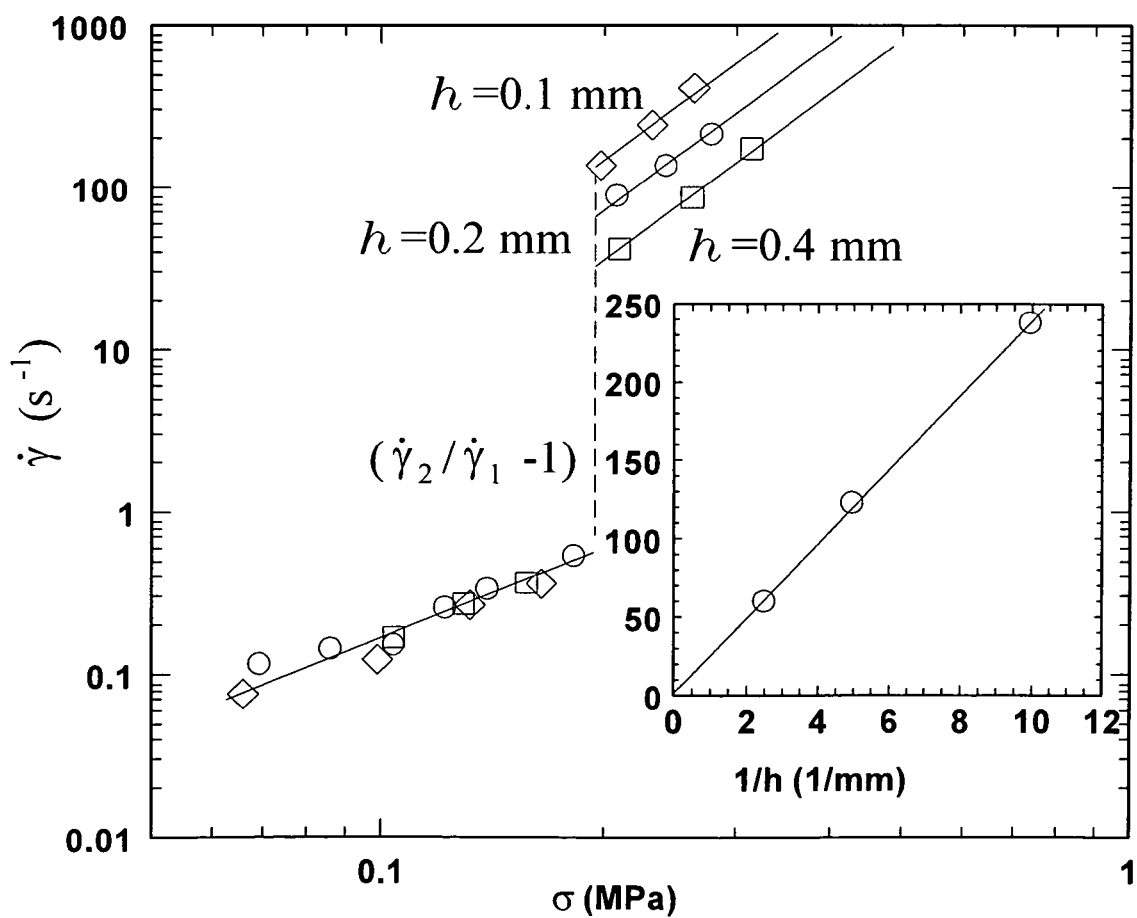
FIG. 7 is a graph of the discontinuous flow transition examined with three different gap sizes as indicated for PBD (207 Kg/mol), at T=25° C., where the inset shows that the abrupt jump in the nominal shear rate as characterized by the ratio $(\dot{\gamma}_2/\dot{\gamma}_1-1)$ varies linearly with 1/h in agreement with Equation 2.

One of the important characteristics of interfacial wall slip is the gap dependence of the slip correction as anticipated by Equation 2. In one demonstration of the present invention, three different gap distances are used to show that the transition magnitude indeed changes linearly with 1/h. FIG. 7 reveals a clear variation of the jump in the nominal shear rate with the gap distance h. Specifically, the inset in FIG. 7 shows a straight line relating the shear rate ratio and reciprocal gap thickness.

Figure 8:
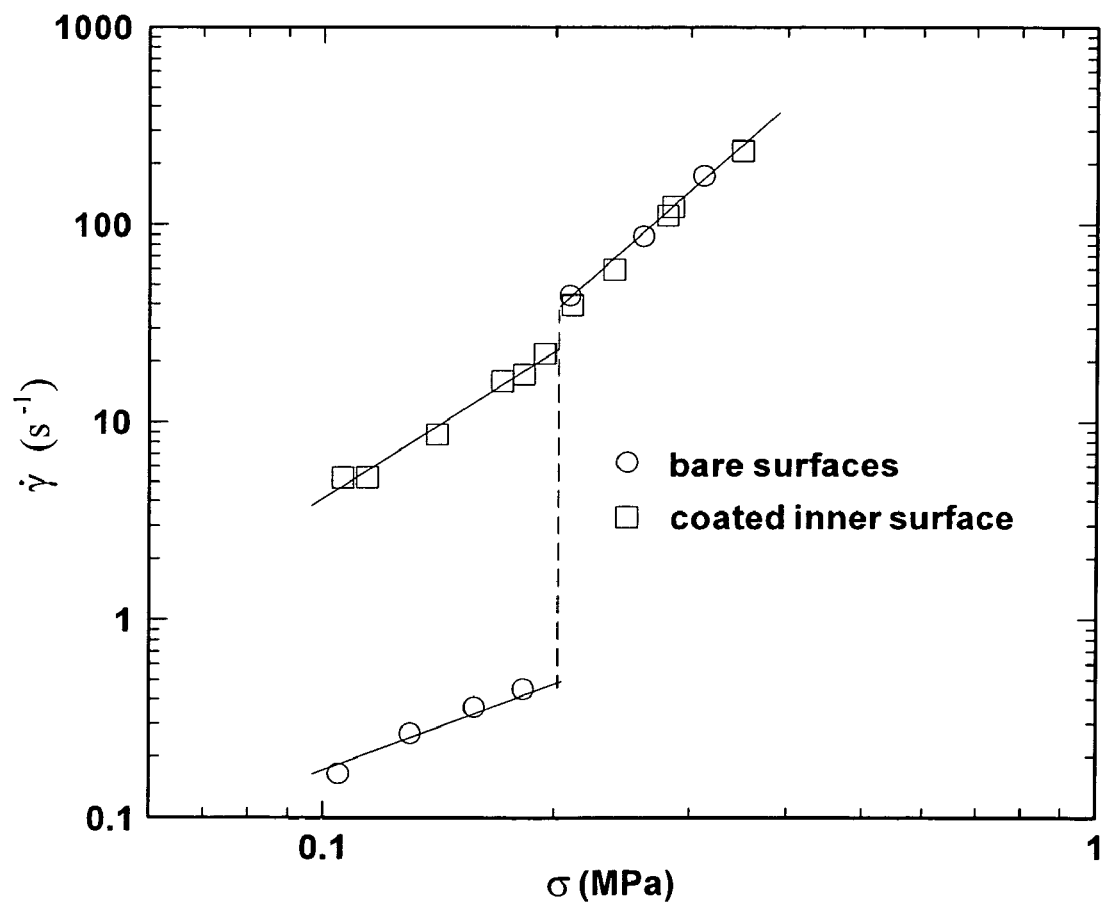
FIG. 8 is a graph showing the effect of causing wall slip to occur adhesively throughout the applied stress range, leading to the removal of the stick-slip transition observed with the bare cylinder surfaces, where the gap distance h was 0.4 mm for PBD (207 Kg/mol), at T=25° C., and the remaining small jump (in the squares) around 0.2 MPa resulted from the stick-slip transition taking place on the outer cylinder wall that was without coating.

Another demonstration of an embodiment of the present invention shows that the observed transition is interfacial rather than constitutive in nature. According to this example, one of two inner shearing surfaces is coated with a layer of polysiloxane to make it non-adsorbing. If the observed flow transition diminishes or does not take place in the shear cell with the surface coating, then this supports that the phenomenon is interfacial. FIG. 8 shows that the surface coating results in massive wall slip to occur through stress-induced desorption. Since only one of the two surfaces was coated, the squares in FIG. 5 would not merge with the circles on the upper slip branch until the stick-slip transition also took place on the bare surface of the outer cylinder around 0.2 MPa, which is expected from FIGS. 2 and 4.

Polymer chains in the bulk can be different from those at melt/wall interfaces. The melt/wall interface can comprise a monolayer of adsorbed chains. From the point of view of the adsorbed chains, simple shear flow is as effective in causing chain deformation as extensional flow. Thus, a first-order discontinuous flow transition involving interfacial slip can be predicted. In some examples involving monodisperse PBD, the SST actually takes place at an applied stress equal to about 0.2 MPa where the PBD chains in the bulk of these samples have hardly experienced any significant deformation $\gamma$ where $\gamma$ is roughly $\sigma_c/G_N^0$, which is equal to about 20% when the plateau modulus $G_N^0$ is taken to be about 1.0 MPa. This example is consistent with the idea that tethered chains undergo much greater deformation than the free chains in the bulk, and undergo a disentanglement transition resulting in the SST.

According to some embodiments, a constitutive bulk flow transition can also occur as a result of an entanglement-disentanglement transition (i.e. a bulk SST). While not wishing to be bound to any one theory, an interfacial SST might supersede any bulk constitutive transition because the tethered chains can orient more effectively than the bulk free chains. Assuming it takes place at all, a bulk flow transition would occur at a shear stress higher than the critical stress $\sigma_c$. It is uncertain whether a yield-like constitutive transition would occur for entangled polymer melts. However, some logical extrapolations of the flow behavior observed in entangled solutions anticipate such constitutive transitional flow behavior. Some embodiments of the present invention are adapted to allow measurements at cryogenic temperatures so that these PBD samples flow sufficiently slowly on the upper flow branch.

A constant-force piston shear rheometer (CFPSR) embodiment of the present invention is adapted to enable rheometric studies of polymer melts in simple shear. It comprises two stainless steel concentric cylinders acting as the two shearing surfaces. As illustrated in FIG. 1a, the inner cylinder is adapted to move according to any predetermined force, and its velocity V is monitored with a linear variable differential transformer (LVDT). According to some embodiments, the outer cylinder can be made of two semi-cylinders for easy sample loading. Furthermore, the outer cylinder can have any suitable diameter in view of the overall dimensions of the CFPSR. Some embodiments are equipped with inner cylinders, or pistons, having one of three diameters providing gap distances of h=0.1, 0.2, and 0.4 mm. Some embodiments produce identical flow curves for the monodisperse melts in the Newtonian region when compared with results from a Monsanto automatic capillary rheometer (MACR).

For comparison, a pressure-controlled MACR is employed to provide capillary rheometric characterization of the stick-slip transition phenomenon, and to provide a benchmark. The nominal wall shear rate $\dot{\gamma}$ is calculated according to $\dot{\gamma}=32Q/\pi D^3$ without the Rabinowitsch correction. The nominal wall shear stress $\sigma$ is computed from the applied pressure P according to $\sigma=(D/4L)P$ without the Bagley correction. For the slow-flowing high molecular weight samples, the flow rate Q is estimated according to $Q=M/\rho t$ by collecting and weighing the extrudate, where m is the mass of the extrudate, $\rho$ is the density of the extrudate (0.9 g/cm$^3$) and t is the time of collection. All the measurements are carried out at room temperature, i.e. around 25° C.

According to one embodiment used to illustrate the foregoing measurement, it is necessary to estimate the gap distance h between the co-cylinders instead of using the prescribed values of h. The shear stress is calculated according to the total force F exerted on the piston, as $\sigma=F/A$ (i.e., the force applied to the surface area A of the sample). The weight W of the sample is pre-measured so that its volume $\Omega$ is determined according to $\Omega$=W/$\rho$. The gap distance is estimated according to h=$\Omega$/A=$\Omega\sigma$/F. On the Newtonian branch, we know the sample viscosity $\eta$ from both dynamic shear measurements and capillary rheometry, which is related to shear stress $\sigma$ according to $\eta$=$\sigma$h/V where V/h is the shear rate. Thus, by the readings of F and V and knowing $\Omega$ and $\eta$, we have $$h = (\Omega \sigma V/F)^{1/2} \quad (3)$$

that can be directly computed for any given loading. Typically, the gap distance estimated according to Equation 3 is larger than the preset value by anywhere between 0 and 15%.

The consequence of an interfacial stick-slip transition (SST) in terms of the measured V on the piston is illustrated in FIG. 1b. The piston velocity is $V_1$ before the SST and $V_2$ upon the SST. Thus the jump in V or in the apparent the shear rate V/h at the SST is given by $$V_1/V_2 = \dot{\gamma}_2/\dot{\gamma} = 1 + 2b/h \quad (4)$$

where the Navier-de Gennes extrapolation length b has the geometric meaning as shown in FIG. 1b, and is related to the slip velocity $V_s$ according to b=$V_s$/($V_1$/h).

A bubble-free film of samples is prepared by solution casting and pressing with CRAVER to produce uniform thickness. The evaluations used linear 1,4-polybutadiene (PBD) of various molecular weights, a four-arm star of PBD, and linear 1,4-polyisoprene (PIP) of various molecular weights. These materials are a series of high molecular weight monodisperse linear PBD and PIP compounds. Some relevant characteristics of these samples are set forth in Tables 1 and 2. A sample having sufficient length l and thickness d to produce the desired final dimensions is place on the inner piston (e.g. L equal to about 3 cm and h equal to about 0.02 cm, with L/h equal to about 150). Then the two outer semi-cylinders are assembled, squeezing the sample in the gap. The sample generally flows in the lengthwise direction. Some material will creep into the joint of the two semi-cylinders. Therefore, the outer cylinder is opened up, the joint is cleaned, and the semi-cylinders are reassembled so that the actual gap does not deviate severely from the preset value of the gap distance h. All the measurements are carried out at room temperature around 25° C.

According to some embodiments, the inner piston is coated with a polysiloxane elastomer to diminish or eliminate polymer adsorption. This solid layer of coating can be formed by injecting a 15wt % isopropyl acetate solution of a siloxane copolymer (e.g. Permalon# M-15, Russell Products Co., Inc.) onto the preheated surface and then allowing it to cure at about 180° C. for about one hour.

Melt flow behavior in simple shear under controlled shear force conditions includes several important effects. These effects include molecular weight dependent flow characteristics, and effects related to the polymer chain structure.

As discussed with regard to FIG. 1b and Equation 4, the discontinuous increase in the apparent shear rate V/h can be described by the Navier-de Gennes extrapolation length b, which is proportional to the bulk shear viscosity $\eta$ according to $$b = (\eta/\eta_i)a = (M_w/M_e)^{3.4} a \quad (5)$$

The slip layer has a thickness comparable to the tube diameter a. Thus, according to Equation 5, during SST the slip layer has a viscosity $\eta_i$ equal to that of an un-entangled melt that has an entanglement molecular weight $M_e$. The second equality follows from the empirical relationship that $\eta$ is directly proportional to $M_w^{3.4}$ for relatively monodisperse samples. This molecular scaling does not hold if there is significant pre-transitional wall slip due to less-than-perfect polymer adsorption, nor would it hold for the molecular weight dependence of b involved in the pre-transitional wall slip. Evaluating b using the rate-controlled mode requires evaluation at two different gaps involving the same shear stress $\sigma$. Since $\sigma$ would oscillate in the strong slip regime (i.e., the spurt window), it is an difficult to quantify b in the flow oscillation. This is why the previous determination of b could only be done below the spurt transition and no scaling of b$\propto$$(M_w)^{3.4}$ could be confirmed in strain-controlled sliding plate rheometry. Some embodiments that include a strain-controlled sliding plate rheometer do not lead to discontinuity in the observed shear rate V/h.

In some embodiments simple shear is generated with a constant force or shear stress so that the shear rate V/h or the plate velocity V can take whatever value results from the melt's flow response to the applied force. Using a CFPSR consistent with the above description, the simple shear behavior of highly entangled polymer melts at high stresses can be examined. Flow curves shown in FIG. 2 are based on the model melts of linear 1,4-polybutadiene (PBD), showing a stick-slip transition (SST) around $\sigma$=0.2 MPa independent of molecular weight, in agreement with capillary rheometric measurements. As shown in FIG. 3, the magnitude of the SST characterized by b scales linearly with sample viscosity $\eta$ and molecular weight $M_w$, of four monodisperse samples. This confirms the scaling prediction that results from Equation 5. Moreover, taking the entanglement molecular weight $M_e$ to be about 2000 g/mol for PBD and a as an interfacial layer thickness of about 4 nm, b is found from Equation 4 to be on the same order of magnitude as observed experimentally in FIG. 2.

The data in FIG. 2 both show the overlapping of the upper slip branch for the different molecular weights. While not wishing to be bound to anyone theory, this overlap can be explained by the following. For large-magnitude SSTs, b/h>>1. Therefore, Equation 5 becomes $$\dot{\gamma}_2 \cong \dot{\gamma}_1 (2b/h) = (\sigma/\eta)(2\eta/\eta_i)(a/h) = (2\sigma_c/\eta_i)(a/h) \quad (6)$$

which is independent of $\sigma$, i.e., of M, and is determined by the viscosity $\eta_i$ and thickness a of the slip layer for a given h.

Figure 4:
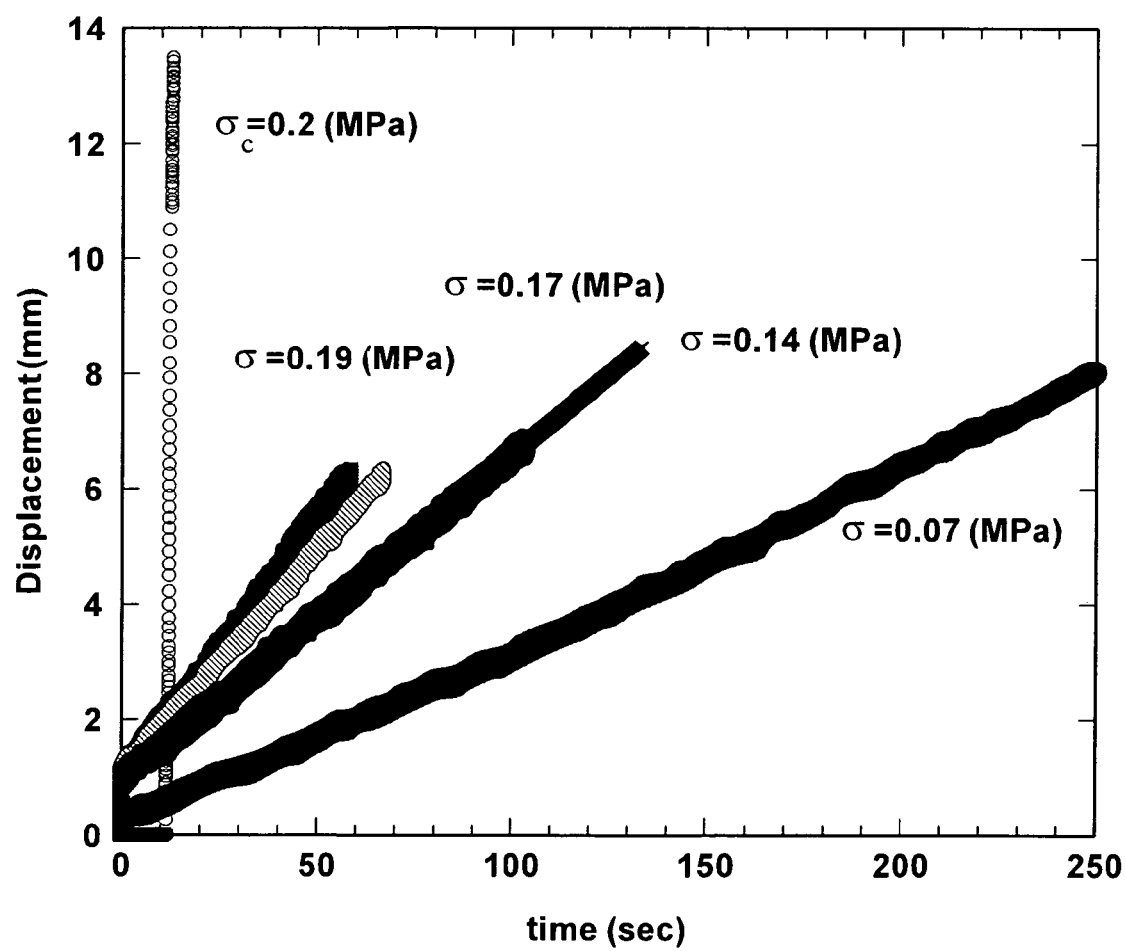
FIG. 4 is a graph of the displacement of moving inner piston (mm) as a function of time (sec) in different stress level from 0.07 to 0.2 (MPa) for PBD (207 Kg/mol), where the gap is about 0.2 mm at T=25° C., and shows the displacement of moving inner piston (mm) versus time (seconds) in $\sigma_c$=0.2 (MPa) in lower Newtonian branch and upper branch in the same level of $\sigma_c$ for PBD (207 Kg/mol), where the gap is about 0.2 mm at T=25° C.

The data in FIG. 2 can be obtained by applying discrete values of forces to the piston and using an LVDT to measure the displacement of the piston as a function of time. FIG. 4 shows displacement as a function of various applied stresses for the 200 Kg/mol sample. At the critical stress, the piston initially moved very slowly corresponding to flowing on the no-slip branch until a sufficient amount of strain has been experienced by the sample so as to result in a SST. Thus, the piston velocity suddenly jumped substantially as shown in FIG. 4.

Figure 5:
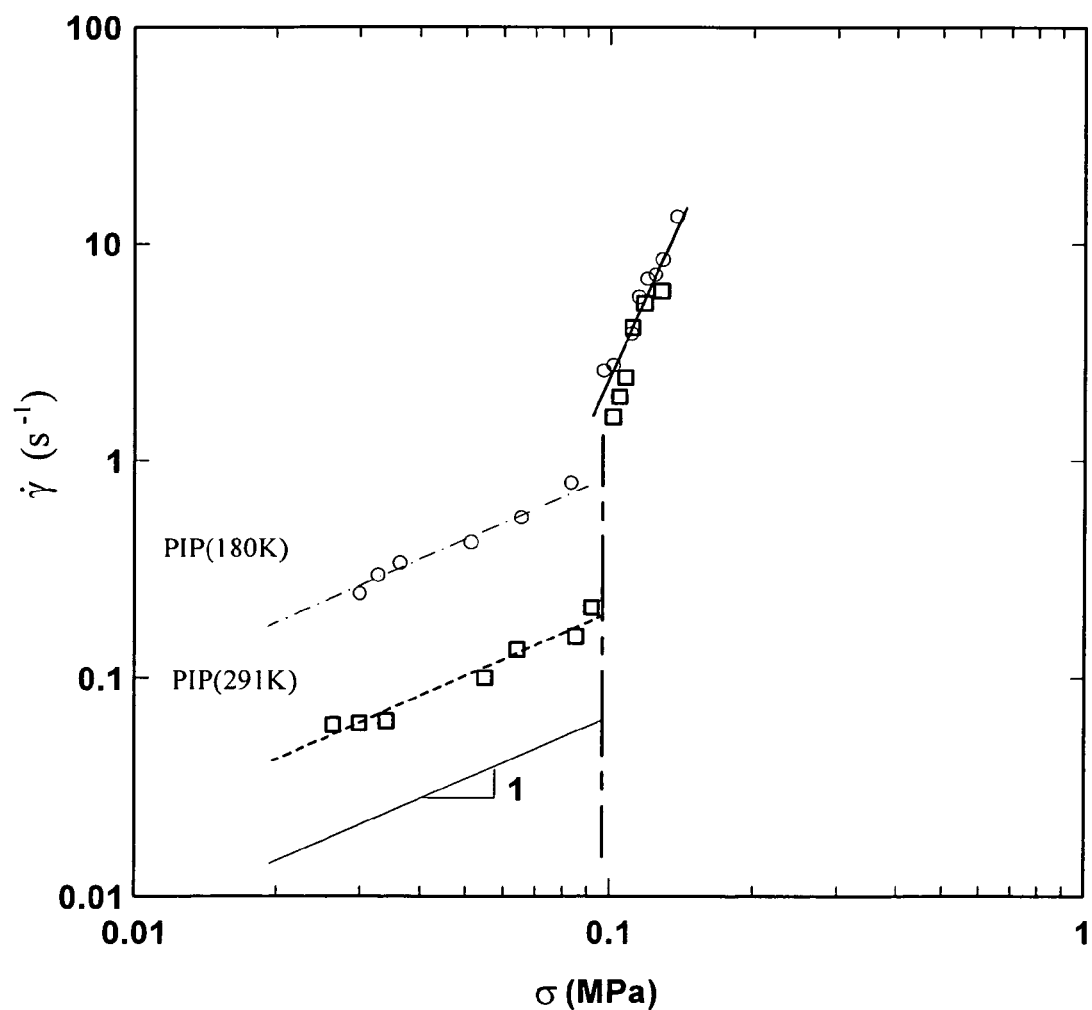
FIG. 5 is a graph of the nominal shear rate, evaluated according to $\dot{\gamma}=V/h$, as a function of the applied shear stress for three 1,4-polyisoprene (PIP) samples of increasing molecular weight (M=150 to 300 Kg/mol), where the gap distance h is around 0.2 mm at T=25° C.

The same measurements are carried out for linear 1,4-polyisoprene (PIP) samples. As shown in FIG. 5, the SST occurs for both samples at a lower critical stress of about $\sigma_c$=0.1 MPa. Since the entanglement molecular weight $M_e$ for PIP is twice as high, the plateau modulus of PIP is lower by a factor of two than that of PBD, leading to a lower critical stress $\sigma_c$.

Figure 6:
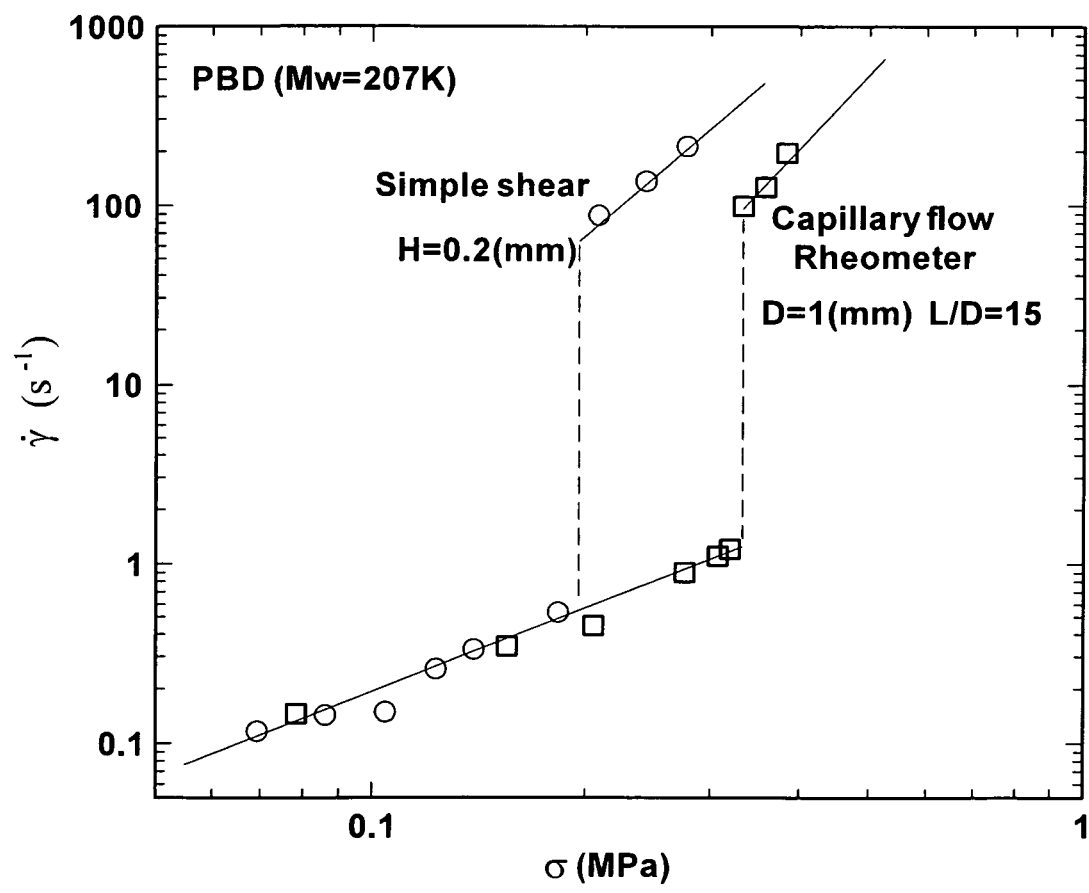
FIG. 6(a) is a graph of the comparison between flow curves obtained with the present constant-force shear rheometer and a capillary rheometer, where the gap h is around 0.2 mm and capillary die diameter D=1.0 mm with the aspect ratio L/D=15 for PBD (207 Kg/mol), at T=25° C.
FIG. 6(b) shows a comparison between flow curves obtained with the present constant-force shear rheometer and a capillary rheometer, where the gap h is around 0.2 mm and capillary die diameter D=1.0 mm with the aspect ratio L/D=15 for PIP (207 Kg/mol), at T=25° C.
Figure 6:
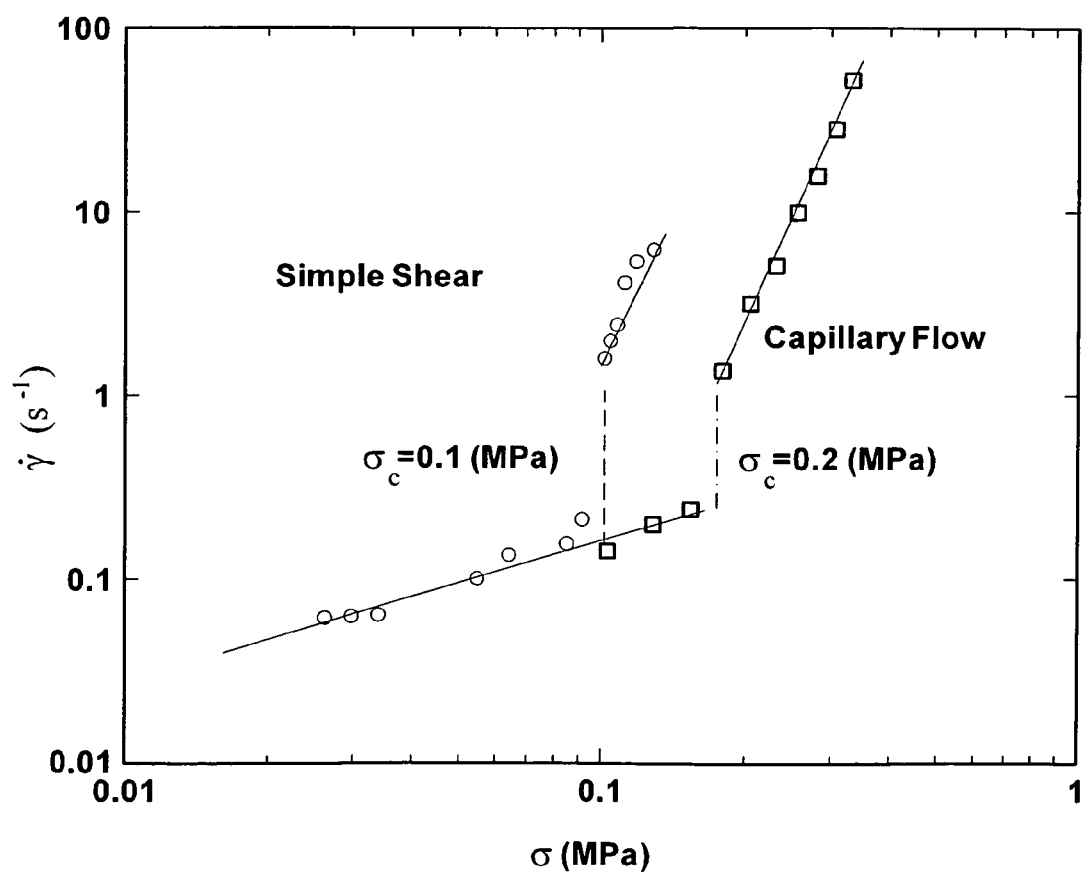

A comparison between the flow curve obtained with one embodiment (CFPSR) versus that of a capillary flow Rheometer is shown in FIG. 6a. According to this embodiment the die has a diameter D=1.0 mm and aspect ratio L/D=15. FIG. 6a shows that the 200 Kg/mol PBD melt undergoes an abrupt transition in both planar Couette shear and pressure-driven capillary flow. Thus, the transitional characteristic is not unique to capillary flow. Since the two rheometric methods should measure the same shear rate at sub-critical stresses ($\sigma<\sigma_c$), the sub-critical region can be used to provide a mutual point of reference between the two rheometers. More interestingly, the critical stress $\sigma_c$ is significantly higher for capillary flow. Since the lower Newtonian branches overlap well for both flow apparatuses, the difference in $\sigma_c$ is real and must be taken seriously. The same comparison between drag flow and pressure-driven flow is carried out for PIP (291 Kg/mol). Again the simple shear apparatus shows a considerably lower $\sigma_c$.

A high level of hydrostatic pressure P, on the order of $P=(4L/D)\sigma_c=1.2\times10^7$ Pa, is present in capillary die flow measurements. Thus, most of the die length feels a hydrostatic pressure on the order of $10^7$ Pa. While not wishing to be bound by any one theory, the hydrostatic pressure appears to defer the onset of the SST, i.e. increase $\sigma_c$. These results suggest that chain adsorption is stronger under high hydrostatic pressure because the state of polymer adsorption has a strong effect on the interfacial SST critical stress. Furthermore, prior to the present invention, this observation could not have been made, because only a comparison where the SST occurs under planar Couette shear conditions can reveal this pressure effect.

Figure 9:
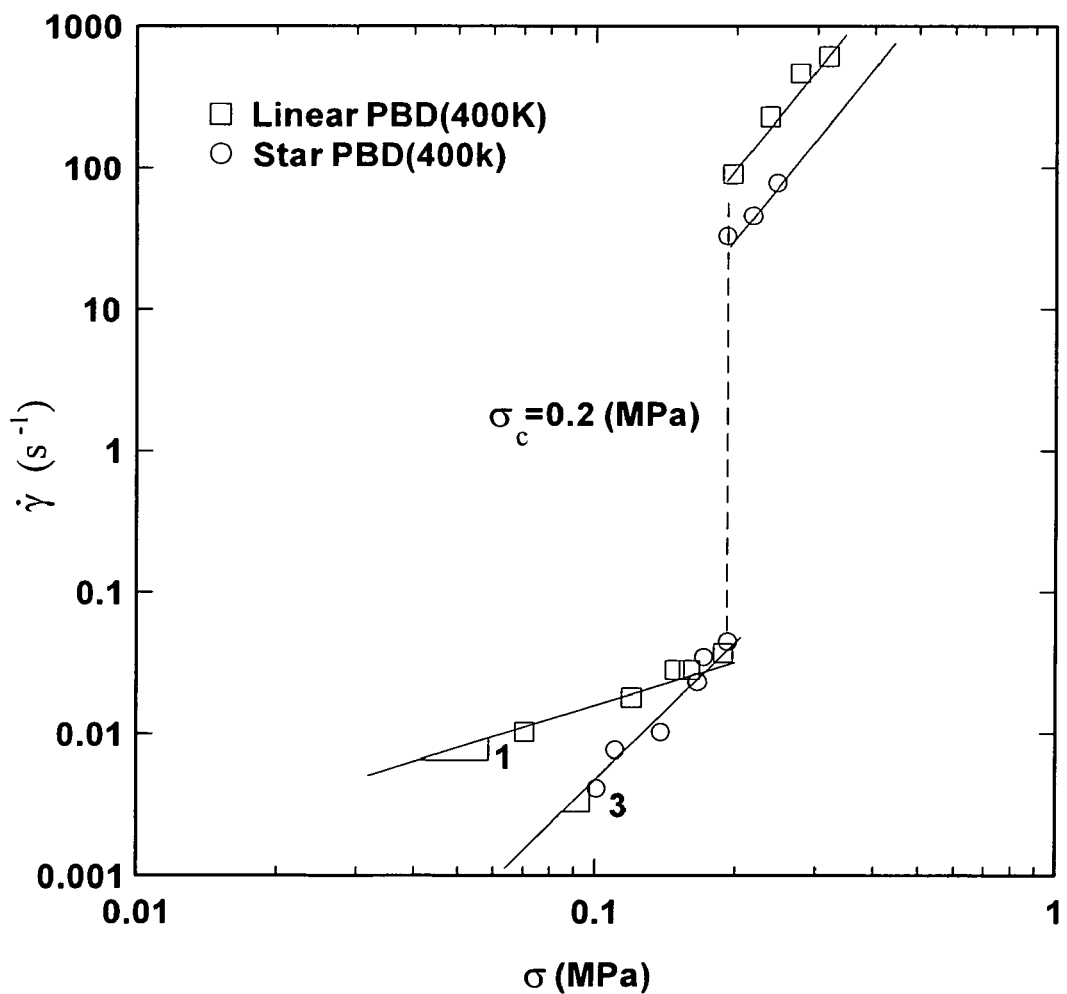
FIG. 9 is a graph of flow curves of linear and star PBD (400 Kg/mol) at T=25° C., where the gap is around 0.2 mm.

In one example the flow behavior of linear and four-arm-star PBD (400 Kg/mol) is studied, as shown in FIG. 9. The SST of both star and linear PBD is observed at the same critical stress, i.e. $\sigma_c=0.2$ MPa. Thus, $\sigma_c$ is independent of chain structure. The no-slip branch of the four-arm star sample is not Newtonian, even at 0.1 MPa. Rather, the four-arm star has a much higher slope of about 3 instead of 1. Surprisingly, the upper slip branches do not emerge, which is contrary to the analysis according to Equation 6. However, this result is confirmed by pressure-driven capillary rheometry. This result suggests slip layer characteristics are independent of chain structure. According to Equation 6, the value of $(a/\eta_i)$ is smaller for the four-arm star PBD than for the linear PBD.

According to this example, the SST takes place at about 0.2 MPa. Since the elastic plateau modulus $G_N^0$ of 1,4-PBD is about 1.0 MPa, the PDB chains in the bulk of these monodisperse samples have hardly experienced any significant deformation $\gamma$ according to $\gamma \approx \sigma_c/G_N^0 = 20\%$. The first layer of unadsorbed chains adjacent to the stationary wall, experience greater strain than the bulk chains. Therefore, they disentangle at a lower shear stress than the bulk chains.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

TABLE 1

Molecular Characteristics of Investigated PBDs.

| Sample | $T_g$ (° C.) | 1-2PBD | 1,4-PBD | $M_n$ (Kg/mol) | $M_w$ (Kg/mol) | $M_w/M_n$ | Source |
|---|---|---|---|---|---|---|---|
| 100K | −100.1 | 8.2 | 91.8 | 98.85 | 99.06 | 1.002 | Goodyear |
| 200K | −100.5 | 8.1 | 91.9 | 207.3 | 207.7 | 1.002 | Goodyear |
| 400K | −99.5 | 7.7 | 92.3 | 410.8 | 411.5 | 1.004 | Goodyear |
| 740K | −99.5 | 10 | 90 | 740 | 750 | 1.07 | Bridgestone |
| four-arm star (400K) | −99.5 | 10 | 90 | 411.2 | xxx | 1.107 | Goodyear |

TABLE 2

Molecular Characteristics of Investigated PIPs.

| Polymer ID | $T_g$ (° C.) | Microstructure (%) | | | Molecular weight (GPC) | | | Source |
|---|---|---|---|---|---|---|---|---|
| | | Cis-1,4 | Trans-1,4 | 3,4- | $M_n$ | $M_w$ | $M_w/M_n$ | |
| 11272-39-4 | −65 | 75.0 | 18.4 | 6.6 | 180K | 190K | 1.06 | Goodyear |
| 11272-39-5 | −65 | 75.2 | 17.8 | 7.0 | 291K | 311K | 1.07 | Goodyear |

I claim:

1. A rheometric device for determining shear rate in an entangled polymer sample that is subject to a stick-slip transition, the device comprising:

a tube having an open end, a closed end, an inside wall and an inside back-wall, wherein the tube comprises two members having semi-circular cross-sections divided along the longitudinal axis of the tube, wherein the tube is capable of receiving a piston at the tube's open end, while maintaining a gap between the inside wall of the tube and the piston, wherein the gap is capable of containing a molten polymer sample;

a means for maintaining the polymer sample in a molten state;

the piston having a first end and a second end, wherein the first end enters the tube before the second end, and wherein the position and/or speed of the piston is monitored;

a means for driving the piston with a known constant force and speed into the tube while the tube contains a molten polymer sample;

a means for recording piston speed and/or position as a function of time; and a means for recording the force applied to the piston.

2. The device of claim 1, wherein the gap is from 0.1 to 0.4 mm thick.

3. The device of claim 1, wherein the means for maintaining the polymer in a molten state comprises a resistive heating element.

4. The device of claim 1, wherein the means for monitoring the speed and/or position of the piston comprises a linear variable differential transformer.

5. The device of claim 1, wherein the means for recording piston speed and/or position as a function of time comprises a computer, microprocessor and/or computer memory.

6. The device of claim 1, wherein the means for recording the force applied to the piston comprises a computer, microprocessor and/or computer memory.

7. The device of claim 1, wherein the piston comprises a material selected from one or more of iron, nickel, and aluminum.

8. The device of claim 1, wherein the tube comprises a material selected from one or more of iron, nickel, and aluminum.

9. A process for making rheometric measurements of entangled polymer samples, comprising:
    loading a polymer sample into the apparatus of claim 1;
    maintaining the polymer sample in a molten state;
    driving the piston into the tube at a known speed and with a known constant applied force, so that the polymer sample is forced to flow into the gap between the piston and the tube;
    calculating the shear rate; and
    recording the shear rate.

10. The process of claim 9, further comprising the step of correcting for a stick slip transition when the applied stress is greater than the predetermined value of the critical stress of the sample, wherein the correction comprises subtracting the effect of the transition from the recorded shear data.

* * * * *